United States Patent
Poulsen (10) Patent No.: US 8,920,365 B2
(45) Date of Patent: Dec. 30, 2014

(54) SEAL FOR A PREFILLED MEDICAL JET INJECTION DEVICE

(75) Inventor: Jens Ulrik Poulsen, Virum (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

(21) Appl. No.: 12/162,614

(22) PCT Filed: Jan. 19, 2007

(86) PCT No.: PCT/EP2007/050548
§ 371 (c)(1),
(2), (4) Date: Aug. 27, 2008

(87) PCT Pub. No.: WO2007/088112
PCT Pub. Date: Aug. 9, 2007

(65) Prior Publication Data
US 2009/0099510 A1    Apr. 16, 2009

(30) Foreign Application Priority Data

Jan. 31, 2006   (EP) ..................................... 06101075

(51) Int. Cl.
*A61M 5/30*    (2006.01)
*A61M 5/31*    (2006.01)
*A61M 5/315*    (2006.01)

(52) U.S. Cl.
CPC ......... *A61M 5/30* (2013.01); *A61M 2005/3103* (2013.01); *A61M 2005/3106* (2013.01); *A61M 2005/3118* (2013.01); *A61M 2005/312* (2013.01); *A61M 2005/31516* (2013.01)
USPC ........................................................ 604/68

(58) Field of Classification Search
CPC ... A61M 5/30; A61M 5/2053; A61M 5/2046; A61M 2005/2013; A61M 5/3007; A61M 2005/3104; A61M 2005/312; A61M 2005/3106; A61M 2005/311; A61M 2005/3103; A61M 2005/3101
USPC .................................................. 604/68–72
See application file for complete search history.

(56) References Cited

U.S. PATENT DOCUMENTS 3,464,412 A  *  9/1969  Schwartz ........................ 604/89
4,010,747 A     3/1977  Clark et al.
(Continued)

FOREIGN PATENT DOCUMENTS

| DE | 10155344 | 5/2003 |
|---|---|---|
| EP | 595508 | 5/1994 |

(Continued)

OTHER PUBLICATIONS

Translated Claims from the Japanese Patent Office for JP 08-509604 Published Oct. 15, 1996.

*Primary Examiner* — Nicholas Lucchesi
*Assistant Examiner* — Weng Lee
(74) *Attorney, Agent, or Firm* — Wesley A. Nicolas; Reza Green; Richard W. Bork (57) ABSTRACT

A sealing membrane 20 on a nozzle 10 for a jet injection device is adapted to seal off the nozzle orifice 12 by having a sealing rim 22 surrounding the nozzle orifice 12, which ensures a distinct closure of the nozzle orifice 12 to protect the nozzle geometry against damage and dirt and to protect the drug 30 contained in the cartridge 10 against contamination. The sealing rim 22 can narrowly enclose the nozzle orifice 12, or in case an adhesive 14 is applied to the nozzle face to ensure skin retention during injection, the sealing rim 22 can run in the middle of the adhesive covered area or entirely outside the adhesive covered area to protect the adhesive as well. A third sealing member 23 can also be provided to give a third distinct closure assurance in case the primary and secondary sealing membrane 20 is damaged. The third sealing member 23 can be one or more plug(s) adapted to press fit inside the nozzle orifice.

7 Claims, 6 Drawing Sheets

(56) References Cited

U.S. PATENT DOCUMENTS

| | | | |
|---|---|---|---|
| 5,087,241 A * | 2/1992 | Mathiesen et al. | 604/20 |
| 6,053,890 A * | 4/2000 | Moreau Defarges et al. | 604/68 |
| 6,102,896 A * | 8/2000 | Roser | 604/218 |
| 6,126,640 A * | 10/2000 | Tucker et al. | 604/187 |
| 6,132,395 A * | 10/2000 | Landau et al. | 604/68 |
| 6,213,980 B1 * | 4/2001 | Colburn et al. | 604/183 |
| 6,258,062 B1 | 7/2001 | Thielen et al. | |
| 6,383,168 B1 | 5/2002 | Landau et al. | |
| 6,409,032 B1 | 6/2002 | Bekkers et al. | |
| 6,883,222 B2 * | 4/2005 | Landau | 29/469 |
| 2004/0162517 A1 | 8/2004 | Furst et al. | |
| 2008/0086079 A1 * | 4/2008 | Williamson et al. | 604/70 |

FOREIGN PATENT DOCUMENTS

| | | |
|---|---|---|
| GB | 705516 | 3/1954 |
| JP | 07255845 A | 10/1995 |
| JP | 07299140 A | 11/1995 |
| JP | 8509604 | 10/1996 |
| JP | 2859833 | 2/1999 |
| JP | 2000-508928 A | 7/2000 |
| WO | WO 96/24398 | 8/1996 |
| WO | 98/13087 | 4/1998 |
| WO | WO 01/47586 | 7/2001 |
| WO | WO 03/015853 | 2/2003 |
| WO | 2005058393 A2 | 6/2005 |
| WO | WO 2005/051465 | 6/2005 |

* cited by examiner

SEAL FOR A PREFILLED MEDICAL JET INJECTION DEVICE

CROSS-REFERENCE TO RELATED APPLICATIONS

This application is a 35 U.S.C. §371 national stage application of PCT/EP2007/050548 (published as WO 2007/088112) filed Jan. 19, 2007 which claims priority under 35 U.S.C. §119 of European Patent Application 06101075.7 filed Jan. 31, 2006, the contents of which are fully incorporated herein by reference.

The invention relates to a medical jet injection device having a nozzle orifice. To assure the integrity of the drug contained in the medical device, or to assure the integrity of the nozzle area of the medical device, the invention concerns a sealing for the medical device.

BACKGROUND OF THE INVENTION

Subcutaneous and intramuscular delivery of liquid drugs by injection is common in the medical arts. As some medications such as insulin must be given frequently by injection to an individual, easy performance of the injections is desirable.

Some patients dislike needle injections due to pain or fear for needles. Further, blood-borne pathogens, such as HIV and hepatitis, can be transmitted to health care workers by accidental needle-sticks. Also, the disposal of used needles is a growing concern. This disposal presents a problem to individuals other than healthcare workers. Children, for example, may find used needles in the garbage, putting them at risk of contracting infection. Discarded needles likewise pose a risk to waste disposal workers.

In efforts to minimize the fears and risks associated with needle injections, several types of needle-free jet injectors have been developed. These devices penetrate the skin using a high velocity fluid jet and deliver medication into the tissue of a patient. In order to accomplish this, a force is exerted on the liquid medication. Jet injectors in general contain a fluid drug which has been transferred into a chamber having a small orifice at one end. The high velocity fluid jet can be achieved for instance by having a drive means, e.g. a ram, accelerated using either a coil spring or a compressed gas energy source. The ram impacts a plunger which in turn creates a high pressure impulse within the chamber. This pressure impulse ejects the fluid medicament through the orifice at high velocity, piercing the skin. The energy source continues to apply a force to the plunger which quickly propels the drug through the opening in the skin, emptying the syringe in a fraction of a second.

The nozzle orifice of a prefilled drug cartridge for a jet injection device requires to be sealed by a protective system to ensure closure integrity of the drug reservoir since it constitutes a primary packaging during storage. The reservoir containing the drug is defined by an inside cavity of the cartridge, and is delimited by the inside cartridge nozzle walls, the plunger in the proximal end of the cartridge sealed towards the cartridge walls, and the distal end of the cartridge penetrated by a nozzle orifice. The orifice opening is the area which poses the highest risk of impurification, spilling or contamination of the drug, since it gives direct access from the environment to the drug contained in the reservoir. Therefore it is of vital importance that a safe and reliant seal of the nozzle orifice is provided.

The nozzle quality is crucial for the system to provide a jet able to penetrate the skin and deliver to the target area of the tissue which is often the subcutis but also other areas. This means that at the time of extrusion of a drug, the nozzle geometry must be unaltered and the nozzle must be clear from any residues from the sealing elements. Therefore any sealing of the nozzle must be removable in a manner that allows reestablishment of the nozzle quality. This poses certain requirements on the protective system.

Also there is a need for a tamper proof feature that clearly signals to the user whether the content of the injection device has been properly protected during storage.

Good performance of jet injection systems can among others be obtained by fixation of the nozzle to the skin to be penetrated. Among the options to do this are vacuum or adhesives where the tip of the cartridge has an adhesive enabled fixation to the skin during injection. In case of an adhesive system, a protective system could be a foil, for instance an alu foil fixed by the skin adhesive. However this can not in all cases be expected to give sufficient aseptic closure integrity due to the relative weak adhesive forces of such a skin fixation system. In these cases a more distinct system is required.

Addressing this problem, U.S. Pat. No. 4,010,747 disclose a needleless injector having at the injection nozzle end a closure member covering the injection opening and the surrounding area. The closure member may be formed of plastic, a wax layer or a varnish layer provided with an adhesive backing. When the closure member is removed, the injection opening is exposed. U.S. Pat. No. 4,010,747 suffers from the mentioned drawback that the sealing system is not sufficiently distinct to give reliable protection of the nozzle area, as the closure member is a relatively crude seal, not specifically designed to locally protect the injection opening. Of course, since the injector is not intended to be prefilled, such a well defined and secure closure integrity is not equally important as it is in one of the embodiments of the present invention. DE 10155344 also describes a closure member for a needleless injector, the closure member being more distinct as it comprises a plug which locally closes the injection opening. The plug is the central member of a closure cap connected to the nozzle area of the injector by a thread-connection. This closure has the disadvantage, that it gives no evidence as to whether the sealing has been tampered or not. There is a risk that the closure could have been dis- and re-mounted prior to use thereby exposing the nozzle area for damage or foreign bodies and potential contaminant of a drug contained in the device. Also, even though the central closure member of DE 10155344 is more distinct, sufficient closure integrity is not ensured, since the sealing is sensitive to the applied closure force of the thread-connection, a parameter difficult to control.

Examples of cap closures for needleless injectors are described in GB 705516, WO 03015853, EP 0595508 and U.S. Pat. No. 6,409,032 (which concerns a break-off closure member for a needleless injector), all of them however lacking a distinct closure of the area local to the injection opening.

In view of the above, one of the objectives of the present invention is to provide a sealing membrane for a medical jet injection device which ensures a safe, well defined distinct closure of the nozzle area local to the injection opening of the device, to acquire protection of the nozzle orifice and contamination repelling storage of a drug contained in the device. A further objective of the invention is to provide a sealing membrane combining the aforementioned objectives with a tamper evident solution, providing user reassurance. Furthermore, an objective of the present invention is to provide a sealing membrane which is simple and easy to use, small and manufactured cost-effectively. It is also an objective to provide a sealing membrane applicable to conventional jet injection devices, contributing to the comfort of the patient, so that the jet injection device can easily be utilized by a non-professional user, e.g. an insulin dependant diabetic.

SUMMARY OF THE INVENTION

In the disclosure of the present invention, embodiments and aspects will be described which will address one or more of the above objectives or which will address objectives apparent from the below disclosure as well as from the description of exemplary embodiments.

In a first aspect, a jet injection unit is provided comprising a nozzle portion with an outlet nozzle orifice adapted to be applied to a skin surface of a subject, and a sealing covering the area of the nozzle adapted to be placed against the skin surface of a subject prior and during an injection. Particular about the sealing is that it comprises a further secondary section, a secondary sealing, adapted to be sealed in a tight manner along a rim going round the nozzle orifice. The closure is thereby restricted to a well defined area of the nozzle face surrounding the orifice thereby allowing for consistent, controllable quality of the sealing and enabling the critical part of the nozzle to be and stay sterile. The cover material and the sealing process can be of any suitable kind, for instance a cover of aluminum foil and a heat sealing. The important matter is that the sealing is distinct, forming a well defined locally delimited sealing around the injection opening, as this is the precondition for the sealing process to be validated and the sealing to be quality controllable.

In a second aspect, the secondary sealing also comprises a sealing member, which can be in the form of bulb or a plug or the like (hereafter called the plug), giving an even more distinct closure of the nozzle orifice. The plug is adapted to provide a third sealing additional to the primary and secondary sealing. The plug has an outer dimension and sufficiently compressible material characteristics to press fit inside the nozzle orifice. The plug seals off the inner cavity of the cartridge containing a drug, thereby protecting the drug against contamination even in the event where the primary sealing member is damaged with the risk of ingress. Advantageously the plug is fixed to the primary and secondary sealing which makes the handling simple, as the plug will be removed simultaneously with the primary and secondary sealing e.g. the sealing membrane.

In a further aspect, the sealing cooperates with the nozzle area adapted to be placed against the skin surface of a subject. As described in the background of the invention, performance and safety of a needle-free injector can be increased when fixation of the injector relative to the skin is ensured. In case this is achieved by applying an adhesive to the mentioned nozzle area, the adhesive must be protected if the desired adhesion shall be obtained. When using a sealing according to this invention, two desired objectives can be reached in combination, the adhesive provided to give good retention of the skin during injection is protected until desired use, and sealing integrity is assured by sealing the secondary sealing member along a rim going round the nozzle orifice and optionally also combined with a third distinct sealing member e.g. a plug. When combining the primary and optionally the secondary sealing member with the protection of an applied adhesive, a range of possible embodiments is available comprising the following: The distinct sealing rim can run within the adhesive ring, leaving no access for the drug to the adhesive during storage. The distinct sealing rim can run in the area between an inner adhesive covered area adjacent to the nozzle orifice and an outer adhesive covered area along the perimeter of the nozzle area, thereby allowing the adhesive to work as close to the nozzle orifice as possible. Further the distinct sealing rim can run on the outside perimeter of the adhesive covered area, giving the best protection of both the nozzle orifice and the adhesive.

As used herein, the term "drug" is meant to encompass any drug-containing flowable medicine or medicament capable of being passed through a nozzle under high pressure, such as a liquid, solution, gel or fine suspension. Representative drugs include pharmaceuticals such as peptides, proteins, and hormones, biologically derived or active agents, hormonal and gene based agents, nutritional formulas and other substances in both solid (dispensed) or liquid form. In the description of the exemplary embodiments reference will be made to the use of insulin.

DESCRIPTION OF THE DRAWINGS

In the following the invention will be further described with references to the drawings, wherein.

In the figures like structures are generally identified by like reference numerals.

DESCRIPTION OF EXEMPLARY EMBODIMENTS

When in the following terms as "distal", "proximal" and "radial" or similar relative expressions are used, these only refer to the appended figures and not necessarily to an actual situation of use. The shown figures are schematic representations for which reason the configuration of the different structures as well as their relative dimensions are intended to serve illustrative purposes only.

Figure 1:
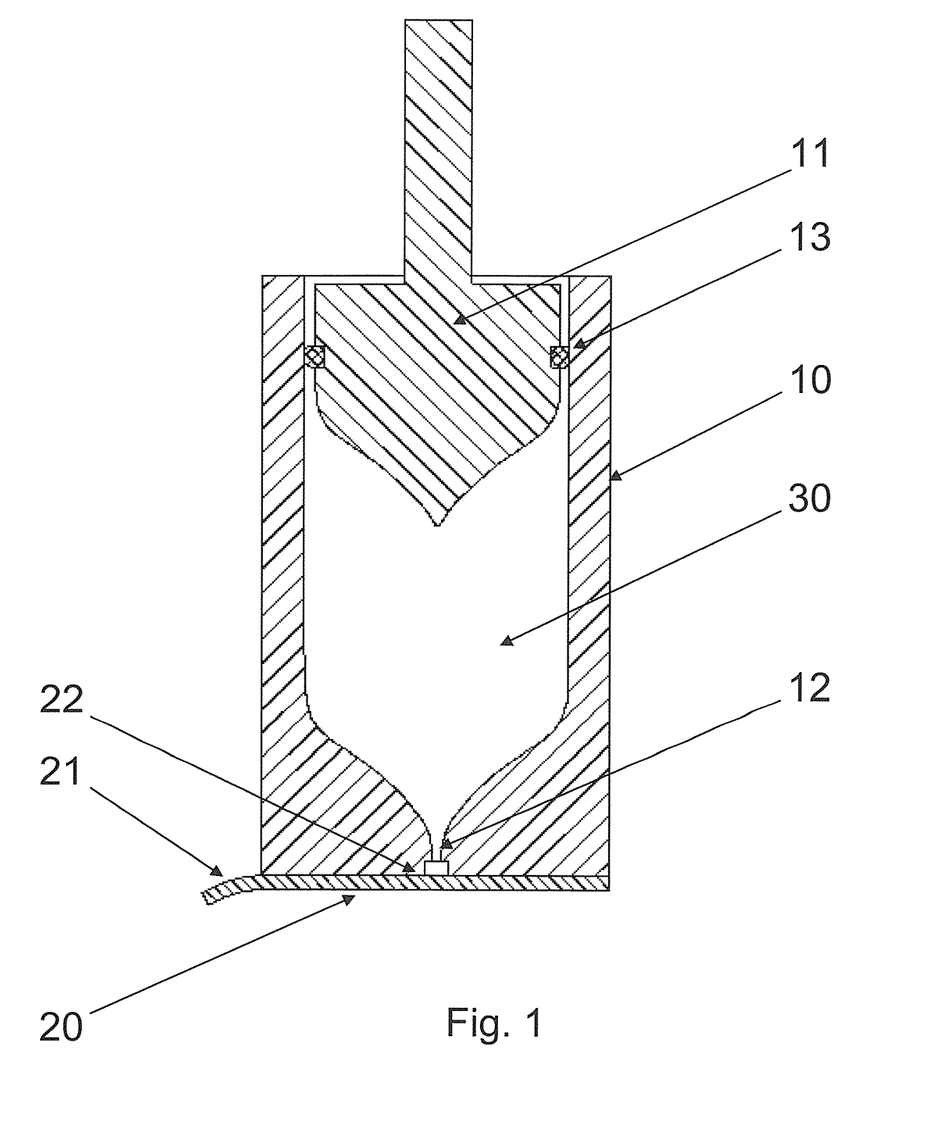
FIG. 1 shows a sectional view of the lower part of a jet injection unit and a sealing membrane.

FIG. 1 shows a sectional view of the lower part of a jet injection device. It comprises a hollow cartridge 10 with a nozzle orifice 12 and a plunger 11 with a sealing ring 13 of any conventional kind. Together, the inside cavity of the cartridge 10 and the plunger 11 together with the sealing ring 13 defines a volume which can contain a drug 30. The foremost end of the plunger 11 has a shape corresponding the shape of the inside end of the cartridge 10, as can be seen on the figure. The corresponding shapes ensure that when the plunger 11 is moved forward in the cartridge 10, when performing an injection, only a small volume of drug 30 is left to waste in the cartridge 10. To ensure sealing integrity of the nozzle orifice 12, the nozzle face adapted to be held against the skin of a subject prior to and during an injection, and the drug 30 contained in the cartridge, a sealing membrane 20 is provided, designed for interaction with the injection device. The sealing membrane 20 is covering the nozzle orifice 12 and the nozzle face and it has a distinct closure (the secondary sealing) covering and cooperating with the nozzle orifice 12. The secondary sealing may be an integrated part of the sealing membrane 20, as is the case on FIG. 1, the secondary sealing being defined by the distinct sealing rim 22 around the nozzle orifice. The sealing membrane 20 may comprise a flap 21 enabling a user to peal off the sealing membrane 20 prior to an injection. The sealing membrane 20 and the distinct closure (the secondary sealing) may be made of any suitable material, one being aluminium foil, often used for tight sealing of drug containers.

Figure 2:
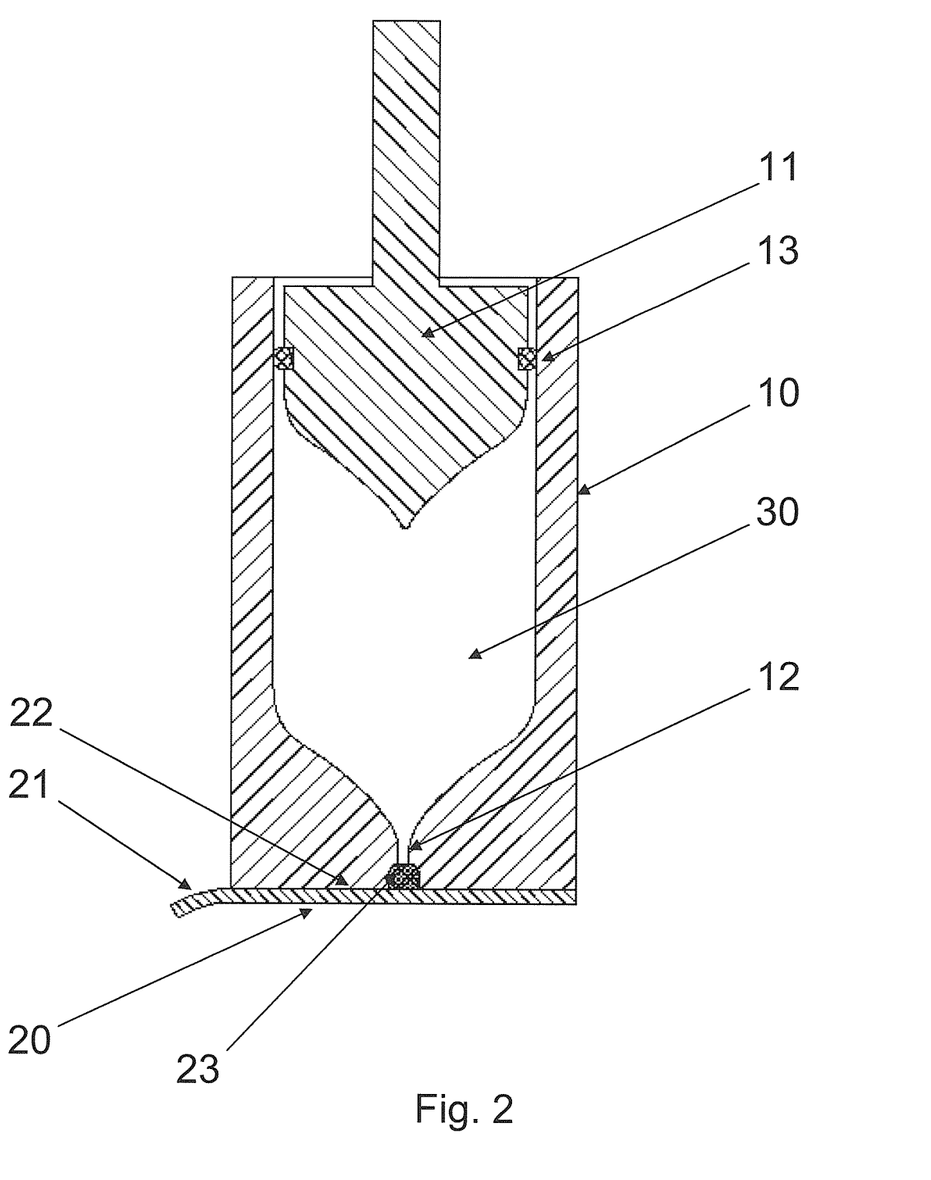
FIG. 2 shows the same sectional view, but with the sealing membrane comprising a plug as third sealing member.

As can be seen on FIG. 2, the distinct secondary sealing may further comprise a sealing member, a third sealing, here a plug 23 adapted to press fit inside the injection opening 12. The plug 23 may be fixed to the sealing membrane 20, whereby it is easily removed simultaneously with the covering sealing membrane 20 prior to an injection.

Figure 3:
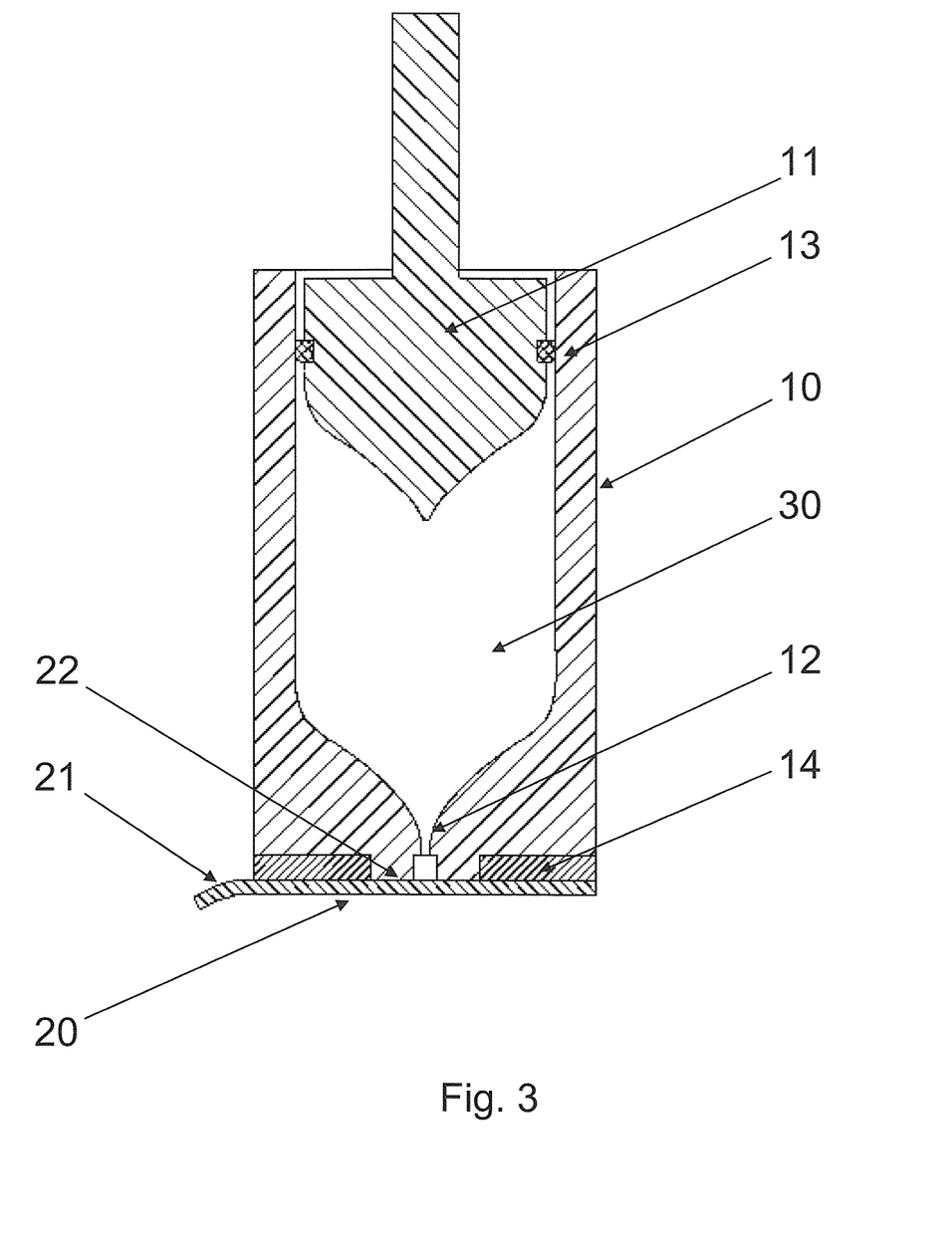
FIG. 3 shows the sectional view where the nozzle face is provided with adhesive on an area surrounding the sealing rim.
Figure 4:
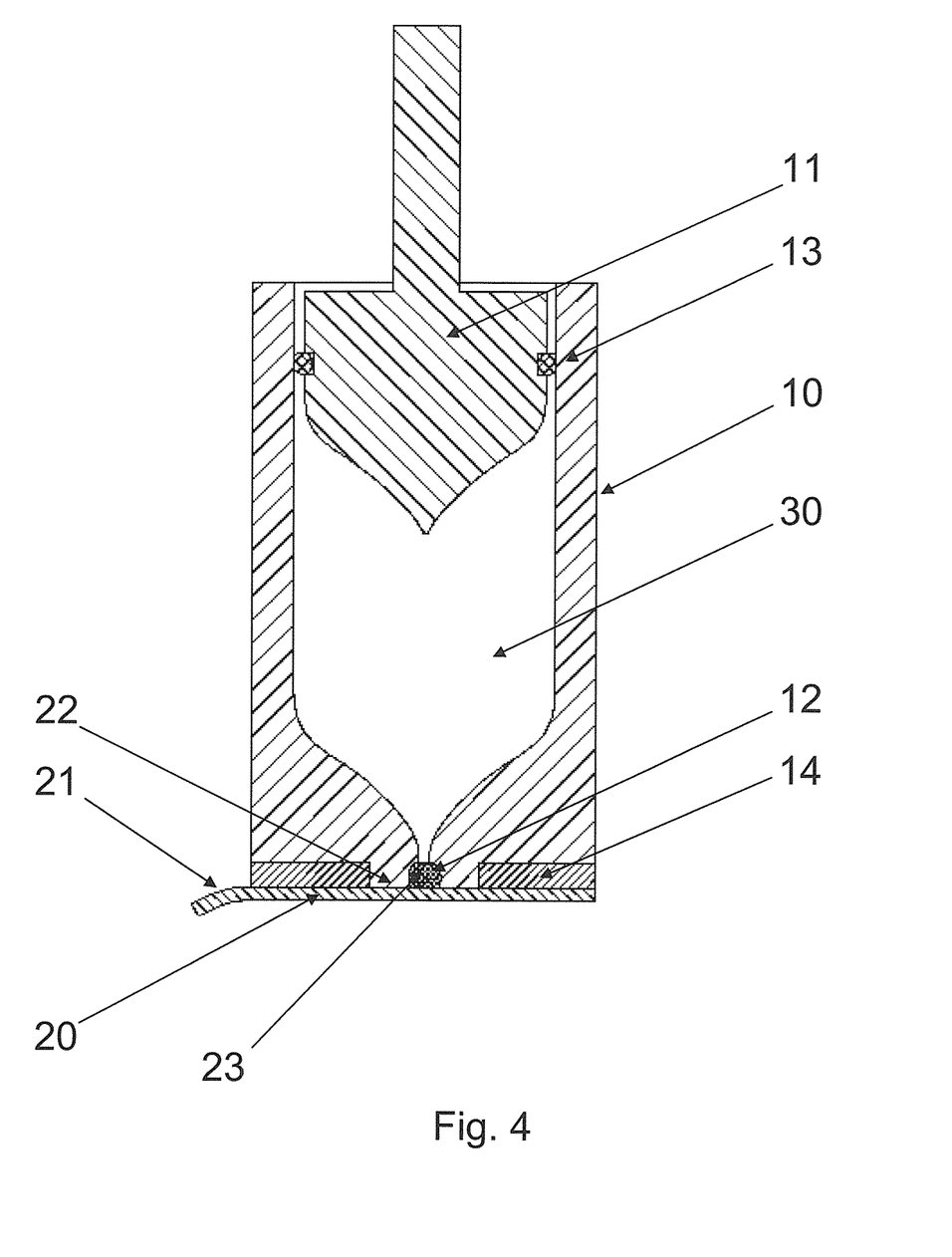
FIG. 4 as FIG. 3, but comprising a plug as third sealing member.

FIG. 3 shows en embodiment where a part of the nozzle face is provided with an adhesive 14 to ensure skin retention during injection. An inner part of the nozzle face is not covered with adhesive 14, thereby leaving an inner area surrounding the nozzle orifice 12 suitable for the sealing rim 22, ensuring a distinct closure in combination with the use of adhesive on the nozzle face. This embodiment can also be used in combination with the third sealing member 23 as can be seen on FIG. 4 where the distinct secondary sealing further comprises a plug 23.

Figure 5:
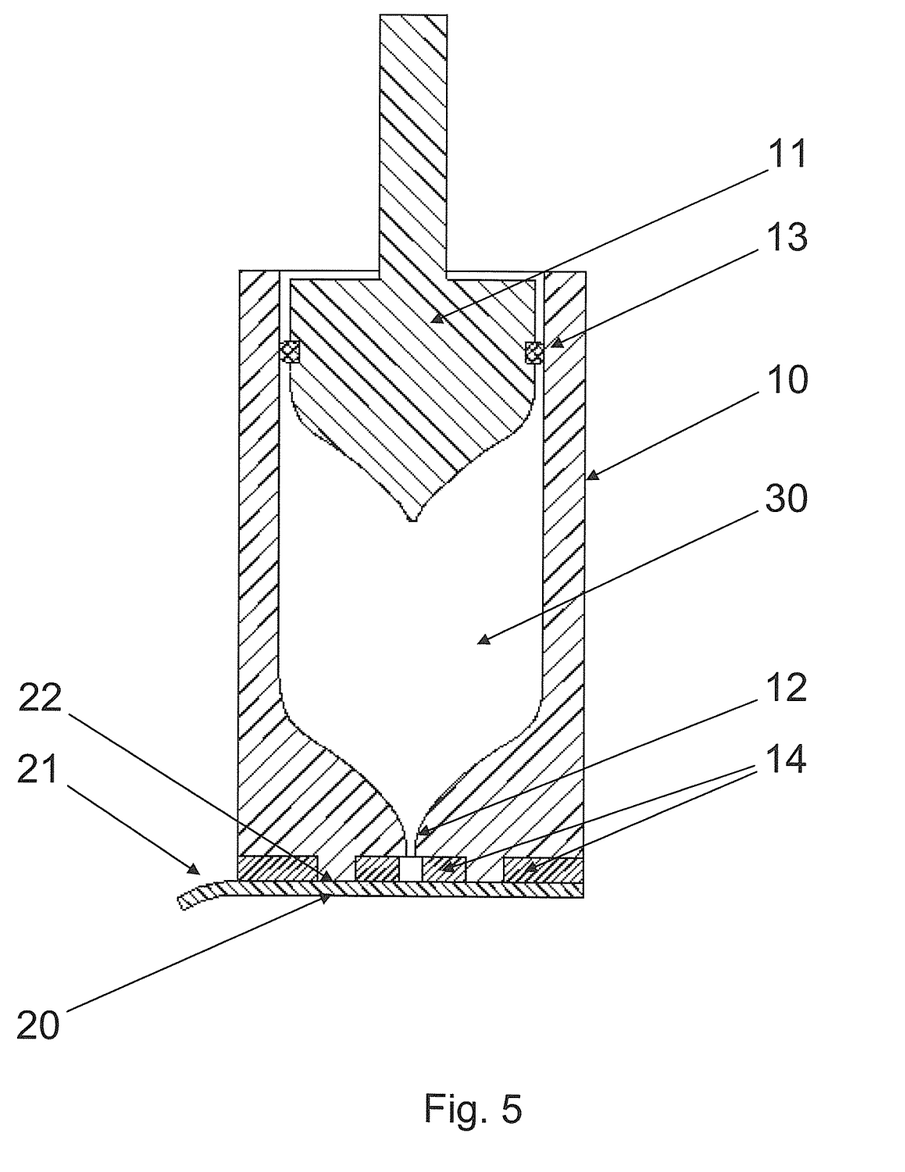
FIG. 5 shows the sectional view with an embodiment where the adhesive provided on the nozzle face is covering an area inside the sealing rim and an area outside the sealing rim.
Figure 6:
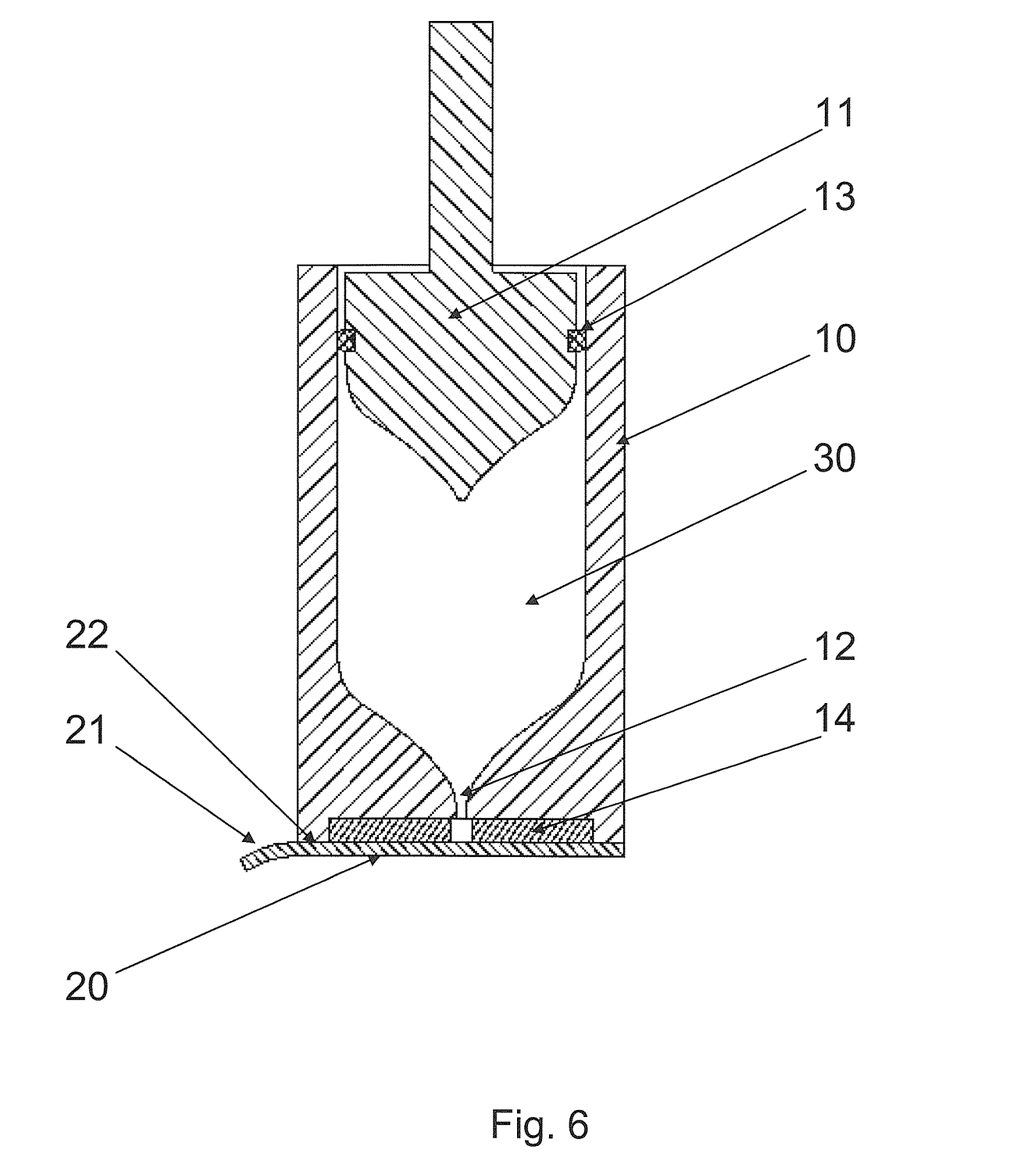
FIG. 6 as FIG. 5, but with the adhesive covered area being entirely surrounded by the sealing rim.

Alternating the location of the sealing rim 22 compared to the adhesive covered area(s) 14 can be used to accomplish different objectives. On FIG. 5 an embodiment is shown where the sealing rim 22 is still of a relative narrow girth, but unlike the embodiment on FIG. 4, the sealing rim 22 leaves room for an adhesive covered area 14 inside the sealing rim 22, which ensures skin retention closest possibly to the injection opening(s) 12. A further embodiment shown on FIG. 6 illustrates how a relatively wide sealing rim 22 can entirely encompass the adhesive covered area (14) which gives a good protection of the adhesive 14.

The invention claimed is:

1. A sealing in combination with a single use prefilled jet injection assembly for a medical jet injection device, comprising:
   the single use prefilled jet injection assembly comprising,
     a dose chamber,
     a nozzle,
     a nozzle face and a nozzle orifice, and
     a first sealing comprising a first sealing adhesive and a sealing membrane, the sealing adapted to cover the nozzle face and nozzle orifice,
   wherein said dose chamber, nozzle, nozzle face and nozzle orifice are integrated to one unit,
   the nozzle face is integrated with a secondary sealing adhesive wherein said secondary sealing adhesive is provided along a rim around said nozzle orifice, and
   wherein when the first sealing is removed from the nozzle face and nozzle orifice, the secondary sealing adhesive remains along the rim around said nozzle orifice.

2. A sealing in combination with a single use prefilled jet injection assembly for a medical jet injection device according to claim 1 wherein the first sealing is a cover material integrated with said sealing membrane.

3. A sealing in combination with a single use prefilled jet injection assembly for a medical jet injection device according to claim 2 wherein said cover material is an aluminium foil heat sealed to the rim around the nozzle orifice.

4. A sealing in combination with a single use prefilled jet injection assembly for a medical jet injection device comprising:
   the single use prefilled jet injection assembly comprising,
     a dose chamber,
     a nozzle,
     a nozzle face and a nozzle orifice, and
     a first sealing comprising a first sealing adhesive and a first sealing membrane, said first sealing adapted to cover the nozzle face and nozzle orifice,
   wherein said dose chamber, nozzle, nozzle face and nozzle orifice are integrated to one unit,
   the nozzle face is integrated with a secondary sealing comprising a second sealing adhesive and a second sealing membrane wherein said secondary sealing adhesive is provided along a rim around said nozzle orifice, and
   the secondary sealing comprising a third sealing member adapted to press fit inside or onto the nozzle orifice, the third sealing member being fixed to the first sealing membrane and removable from the nozzle orifice simultaneously with the removal of the first sealing membrane in a single operation leaving behind the secondary sealing adhesive along the rim around said nozzle orifice.

5. A sealing in combination with a single use prefilled jet injection assembly for a medical jet injection device according to claim 4 wherein the third sealing member is a plug.

6. A sealing in combination with a single use prefilled jet injection assembly for a medical jet injection device according to claim 1, wherein the nozzle face is further provided with an adhesive layer whereby the secondary sealing is pealably attached to the medical jet injection assembly in the area related to the nozzle orifice.

7. A sealing in combination with a single use prefilled jet injection assembly for a medical jet injection device according to claim 2 wherein a sealing rim is located within the area provided with adhesive, thereby not leaving access for the drug to contact the adhesive.

* * * * *